United States Patent [19]

Beumer et al.

[11] Patent Number: 5,837,501
[45] Date of Patent: Nov. 17, 1998

[54] NUCLEIC ACID QUANTITATION BY CO-AMPLIFICATION OF TARGET WITH MULTIPLE INTERNAL CONTROLS

[75] Inventors: Thomas Augustinue Maria Beumer; Marinus Gerardus Johannes van Beuningen, both of Oss; Tim Kievits, Vught, all of Netherlands

[73] Assignee: Akzo Nobel N.V., Arnhem, Netherlands

[21] Appl. No.: 938,499

[22] Filed: Sep. 26, 1997

Related U.S. Application Data

[63] Continuation of Ser. No. 661,340, Jun. 12, 1996, abandoned, which is a continuation of Ser. No. 397,172, filed as PCT/EP94/02295 Jul. 8, 1994 published as WO95/02067 Jan. 19, 1995, abandoned.

[30] Foreign Application Priority Data

Jul. 9, 1993 [EP] European Pat. Off. ............ 93202015.9
Dec. 6, 1993 [EP] European Pat. Off. ............ 93203424.2

[51] Int. Cl.$^6$ .............................. C12P 19/34; C12Q 1/68; C07H 21/04; C07H 21/02
[52] U.S. Cl. ........................... 435/91.2; 435/6; 435/91.1; 435/91.21; 536/24.3; 536/24.31; 536/24.32; 536/24.33
[58] Field of Search .............................. 435/6, 91.1, 91.2, 435/91.21; 536/24.3, 24.31, 24.32, 24.33

[56] References Cited

U.S. PATENT DOCUMENTS 5,476,774 12/1995 Wang et al. .......................... 435/91.2

FOREIGN PATENT DOCUMENTS

| 0 303 459 | 2/1989 | European Pat. Off. . |
| 0 525 882 | 2/1993 | European Pat. Off. . |
| WO 92/01812 | 2/1992 | WIPO . |
| WO 93/10257 | 5/1993 | WIPO . |

OTHER PUBLICATIONS

Stratagene catalog, p. 90, 1993.
Duchmann et al, "Quantitative measurement of human T-cell receptor VB subfamilies by reverse transcription polymerase chain reaction using synthetic internal mRNA standards", DNA and Cell Biol. 12(3):217–225, 1993.
Repp et al, (1995), "Construction of RNA standards for high resolution automatic product analysis in quantitative competitive RT-PCR", Biotechniques 19(1):84–5, 87, 89–90.
McCulloch et al, (1995), "An evaluation of competitor type and size for use in the determination of mRNA by competitive PCR", PCR Meth. App. 4:219–226.
Wang et al, (1990), "Quantitative PCR" in *PCR Protocols: A Guide to Methods and Applications* (Innis et al, Ed.s) Academic Press Inc., San Diego, Ca, pp. 70–75.
Gibco–BRL catalog, (Jul. 1, 1993) pp. 11–14.
Wang et al, (Jun. 1993), "Internal cRNA standards for quantitative Northern analysis", Biotechniques 14 (6):935–6. 938, 940–1.
Becker–Andre et al, (1989), "Absolute mRNA quantification using the polymerase chain reaction (PCR). A novel approach by a PCR aided transcript titration assay (PATTY)", Nucleic Acids Res. 17(22): 9437–9446.
Siebert et al, (1993), "PCR MIMICS: competitive DNA fragments for use as internal standards in quantitative PCR", Biotechniques 14(2):244–6, 248–9.
Wang et al, (1989), "Quantitation of mRNA by the polymerase chain reaction", Proc. Natl. Acad. Sci. 86:9717–9721.
Nedelman et al, (1992), "Quantitative PCR with internal controls", CABIOS 8(1):65–70.
Kinoshita et al, (1992), "Quantification of gene expression over a wide range by the polymerase chain reaction", Anal. Biochem. 206:231–235.
Terouanne et al, (1992), "Quantitative and qualitative analysis of amplified DNA sequences by a competitive hybridization assay", Anal. Biochem. 205:193–199.
Ballagi–Pordany et al, (1991), "Quantitative determination of mRNA phenotypes by the polymerase chain reaction", Anal. Biochem. 196:89–94.
Diviacco et al, (1992), "A novel procedure for quantitative polymerase chain reaction by coamplification of competitive templates", Gene 122:313–320.
Vanden Heuvel et al, (1993), "Construction of recombinant RNA templates for use as internal standards in quantitative RT–PCR", Biotechniques 14(3): 395–398.
B. van Gemen et al., "Quantification of HIV–1 RNA in plasma using NASBA during HIV–1 primary infection," *Journal of Virological Methods,* 43 (1993) 177–188.
M.J. Apostolakos et al., "Measurement of Gene Expression by Multiplex Competitive Polymerase Chain Reaction," *Analytical Biochemistry,* 213:2 277–284 (1993).

*Primary Examiner*—W. Gary Jones
*Assistant Examiner*—Jeffrey Fredman
*Attorney, Agent, or Firm*—Mary E. Gormley; William M. Blackstone

[57] ABSTRACT

The present invention is related to an improved method for the quantification of nucleic acid, which can be performed with a minimal amount of nucleic acid amplification reactions. The method according to the invention for the quantification of analyte nucleic acid in a sample comprises the steps of: adding to the sample different respective amounts of different nucleic acid constructs, each construct being distinguishable from the analyte nucleic acid and capable of being co-amplified with the analyte nucleic acid; subjecting the sample to a nucleic acid amplification procedure, using amplification reagents capable of reacting with both the analyte nucleic acid and the nucleic acid constructs; detecting the relative amounts of amplificates derived from analyte nucleic acid and each nucleic acid construct; calculating the amount of analyte nucleic acid from said relative amounts. Each nucleic acid construct is different; the nucleic acid constructs can be distinguished from one another and from the analyte nuclic acid. The nucleic acid constructs do resemble each other, and the analyte nucleic acid, in that all are capable of reacting with the same amplification reagents.

17 Claims, 12 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: Not Relevant ( i i ) MOLECULE TYPE: other nucleic acid
        ( A ) DESCRIPTION: /desc = "DNA"

( i i i ) HYPOTHETICAL: NO ( x i ) SEQUENCE DESCRIPTION: SEQ ID NO:1:

ATGCAAGGTC GCATATGAGT AA                                        22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: both
        ( D ) TOPOLOGY: Not Relevant ( i i ) MOLECULE TYPE: other nucleic acid
        ( A ) DESCRIPTION: /desc = "DNA"

( i i i ) HYPOTHETICAL: NO ( x i ) SEQUENCE DESCRIPTION: SEQ ID NO:2:

ATAAGCACGT GACTGAGTAT GA                                        22

( 2 ) INFORMATION FOR SEQ ID NO:3:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA Primer"

( i i i ) HYPOTHETICAL: NO ( i v ) ANTI-SENSE: YES ( x i ) SEQUENCE DESCRIPTION: SEQ ID NO:3:

AATTCTAATA CGACTCACTA TAGGGTGCTA TGTCACTTCC CCTTGGTTCT CTCA        54

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA Primer"

( i i i ) HYPOTHETICAL: NO ( i v ) ANTI-SENSE: YES ( x i ) SEQUENCE DESCRIPTION: SEQ ID NO:4:

-continued

AGTGGGGGGA CATCAAGCAG CCATGCAAA                             2 9

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA probe"

( i i i ) HYPOTHETICAL: NO ( i v ) ANTI-SENSE: YES ( x i ) SEQUENCE DESCRIPTION: SEQ ID NO:5:

TGTTAAAAGA GACCATCAAT GAGGA                             2 5

NUCLEIC ACID QUANTITATION BY CO-AMPLIFICATION OF TARGET WITH MULTIPLE INTERNAL CONTROLS

This is a continuation of application U.S. Ser. No. 08/661,340, filed Jun. 12, 1996, now abandoned, which is a continuation of U.S. Ser. No. 08/397,172, filed as PCT/EP94/02295 Jul. 8, 1994 published as WO95/02067 Jan. 19, 1995, now abandoned.

The present invention is related to an improved method for the quantification of nucleic acid. The quantification of nucleic acid can be of great importance in various research as well as diagnostic areas. Quantification of nucleic acid can be an important tool in understanding gene regulation and may also be used in monitoring the effects of therapy. The amount of specific nucleic acid sequences present in a sample, as for example human blood or other bodily fluids, may also provide valuable information with respect to the disease state of persons infected with, for example, a certain virus and the efficiency of treatment with certain medicines.

Various methods for the quantitative amplification of nucleic acid have been described. In WO 91/02817 a method for the quantification of nucleic acid using the Polymerase Chain Reaction (PCR) as amplification technique, is described. This method comprises the addition of a standard nucleic acid segment to a sample, which segment can react with the same primers that are used for the amplification of the unknown quantity of target nucleic acid present in the sample. Following amplification the amount of each of the two PCR products is measured, and the amount of the target segment in the original sample is quantified by extrapolating against a standard curve. The standard curve is generated by plotting the amount of the standard segment produced in a polymerase chain reaction against varying, but known, amounts of the nucleic acid present before amplification.

The addition of other sequences to a sample comprising analyte nucleic acid, which are capable of being coamplified with the analyte nucleic acid, has also been described by Becker and Hahlbrock (*Nucleic Acids Research*, Vol. 17, Number 22, 1989). The method described by Becker and Hahlbrock is a method for the quantification of nucleic acid where different known amounts of internal standard, comprising a nucleic acid sequence that differs from the analyte nucleic acid by just one nucleotide (point mutation) are added to fractions of known volume of a sample containing an unknown amount of analyte nucleic acid and coamplified by PCR with the analyte nucleic acid. Identical portions of total RNA are thus "spiked" with decreasing known amounts of internal standard RNA. By introducing one base change in the internal standard sequence a specific restriction site is created and the mutant sequence is cut with the appropriate restriction enzyme before the sample containing the amplified nucleic acid is applied to an electrophoretic gel. The nucleic acid is quantified by comparing the bands in the gel representing (a part of) the mutant sequence and the analyte nucleic acid. One of the disadvantages of this method is that incomplete digestion of the internal standard by the restriction enzyme might cause inaccuracies in the determination of the amount of nucleic acid present.

Becker and Hahlbrock use the internal standard as a marker in their quantification method where both analyte and marker are non-competitively amplified.

A method for the quantification of nucleic acid, using the addition of a known number of molecules of a nucleic acid sequence, corresponding to the target nucleic acid, to a sample containing an unknown amount of the target nucleic acid sequence has also been described in co-pending co-owned European patent application published under no. EP 525882. The method as described in EP 525882 is based on the principle of amplification of nucleic acid from a sample containing an unknown concentration of wild-type target nucleic acid, to which has been added a known amount of a well-defined mutant sequence. Amplification is performed with one primer set capable of hybridizing to the target as well as the mutant sequence. The competitive amplification described in EP 525882 can be performed with a fixed amount of sample and dilution series of mutant sequence or vice versa.

The above described methods involve the addition of a well defined standard sequence to the amplification mixture. To be able to obtain an accurate and reliable measurement with the above described method many amplification reactions have to be carried out: The sample has to be subdivided in different portions of known quantity to each of which a different, known, amount of standard nucleic acid has to be added. Or, with the method as described in WO 91/02817, a standard curve has to be generated from a dilution series, which is rather laborious and may also result in inaccurate estimations of the amount of nucleic acid present since the actual amplification concerning the target nucleic acid and the amplifications concerning the standard curve are performed separately. Due to the great amount of amplification reactions that have to be carried out in order to be able to determine the amount of nucleic acid in a precise and reliable manner, the above described methods are very laborious and time consuming. The need therefore exists for a method for the quantification of nucleic acid that is less laborious and time consuming. The present invention provides such a method.

The present invention provides a method for the quantification of analyte nucleic acid in a sample comprising the steps of:
  adding to the sample different respective amounts of different nucleic acid constructs, each construct being distinguishable from the analyte nucleic acid and capable of being co-amplified with the analyte nucleic acid,
  subjecting the sample to a nucleic acid amplification procedure, using amplification reagents capable of reacting with both the analyte nucleic acid and the nucleic acid constructs,
  detecting the relative amounts of amplificates derived from the analyte nucleic acid and each nucleic acid construct,
  calculating the amount of analyte nucleic acid from said relative amounts.

With the method according to the present invention different nucleic acid constructs are added to the sample.

Each nucleic acid construct is different; the nucleic acid constructs can be distinguished from one another and from the analyte nucleic acid. The nucleic acid constructs do resemble each other, and the analyte nucleic acid, in that all are capable of reacting with the same amplification reagents. With amplification reagents, among other things, one or more amplification primers are meant, which are capable of hybridizing to the analyte nucleic acid and the nucleic acid constructs. Other amplification reagents are the usual reagents used with amplification procedures like the necessary enzymes, nucleic acid polymerases, used with the different amplification techniques known in the art. The method according to the invention can be used with any kind of amplification procedure, for example the so-called polymerase chain reaction (PCR) as described in U.S. Pat. Nos. 4,683,195 and 4,683,202. Another method for the amplification of nucleic acid is the "nucleic acid sequence based amplification (NASBA)" as disclosed in European Patent application EP 0,329,822.

The nucleic acid constructs used with the method according to the present invention are nucleic acid sequences that resemble the analyte nucleic acid in that they are capable of reacting with the same amplification reagents. Each nucleic acid construct should therefore at least comprise the sequence to which nucleic acid amplification primers used can anneal, which sequence is also present in the analyte nucleic acid. The nucleic acid constructs used with the method according to the invention can be distinguished from the analyte nucleic acid and from each other. This can be achieved by constructing nucleic acid constructs in a such a way that each construct comprises a uniquely distinguishable sequence that is not present in the other nucleic acid constructs used nor in the analyte nucleic acid. Preferably nucleic acid constructs are used wherein the uniquely distinguishable sequence is a randomized sequence, comprising e.g. about 20 nucleotides, thus keeping the length and nucleotide constitution of constructs and analyte nucleic acid the same. In the detection, following amplification of analyte nucleic acid and nucleic acid constructs present in a sample, the different nucleic acid constructs may be measured separately by using different detection probes, each capable of recognizing only one of the unique sequences present in the nucleic acid constructs.

Of course there are other ways in which the nucleic acid constructs can be constructed that will render them unique. However, preferably the nucleic acid constructs should not be mutated in such a way that the amplification is hampered. Preferably, with the method according to the invention, nucleic acid constructs are used that are capable of being amplified with the same efficiency as the analyte nucleic acid, otherwise it is difficult to make an accurate calculation based on the amounts of analyte and construct nucleic acid present in the sample after amplification.

Nucleic acid constructs are polynucleotides that can be prepared by different methods known in the art. Nucleic acid constructs can, for example, be prepared by various recombinant DNA strategies. For instance, new sequences can be introduced in the analyte sequence by digestion of the plasmid containing the analyte sequence with restriction enzymes, thus removing the original sequence and inserting a new sequence that may be prepared on a nucleic acid synthesizer or subcloned from a different plasmid. Complete nucleic acid constructs may also be prepared, using a nucleic acid synthesizer.

The nucleic acid constructs should be added to a sample, containing an unknown amount of analyte nucleic acid, prior to subjecting the sample to an amplification procedure. The sample, to which a known quantity of different nucleic acid constructs are added, should, of course, have a predetermined volume, in order to be able to calculate the concentration of nucleic acid present in the sample later on. The sample has to contain a known volume, or quantity of material, taken from the material in which the amount of nucleic acid should be determined. When the concentration of nucleic acid in a certain test fluid is to be determined, a sample should contain all nucleic acid isolated from a known quantity of the test-material under investigation.

The nucleic acid constructs may be added prior or after subjecting the test fluid under investigation (for example human blood serum) to a procedure for the isolation of nucleic acid. Methods for the isolation of nucleic acid have been described and are known to anyone skilled in the art. Nucleic acid isolation procedures, that may be used to prepare a sample that is to be subjected to the method according to the present invention, have been described in, for example, Maniatis et al., Molecular Cloning, a laboratory manual, Cold Spring Harbor Laboratory. Another method for the processing of nucleic acid containing samples has been described by Boom et al., J.Clin.Microbiol. 28:495–503, 1990.

In a preferred embodiment of the invention the nucleic acid constructs are added prior to isolating the nucleic acids from the quantity of test fluid. In this way the loss of nucleic acid that might optionally occur during the isolation procedure will be reflected in both the resulting amounts of analyte nucleic acid and construct nucleic acid present in the sample. The amount of analyte nucleic acid present in original test fluid under investigation can be calculated directly from the obtained results.

When the nucleic acid constructs are added to a known quantity of test fluid prior to subjecting the test-fluid to a nucleic acid isolation procedure, an isolation control nucleic acid construct can be added to the sample after the nucleic acid isolation procedure has been performed. With the addition of the IC (isolation control) sequence it is possible to determine the efficiency of the nucleic acid isolation procedure. Thus, for each sample the threshold value, can be adjusted to the isolation efficiency. The isolation control construct can be a sequence that differs from the analyte and the other nucleic acid constructs, for example because it comprises a unique sequence, but will preferably be amplified with the same efficiency. The IC can be regarded as another "nucleic acid construct" the difference being that the IC molecules are added after the nucleic acid isolation procedure is performed, while, in this preferred embodiment of the invention, the nucleic acid constructs are added prior to subjecting the test fluid to an nucleic acid isolation procedure. The efficiency of the isolation procedure can be calculated, since a well defined amount of molecules of each nucleic acid construct was added prior to subjecting the test-fluid to a nucleic acid isolation procedure, and a well defined amount of IC molecules was added after the nucleic acid isolation procedure was performed. When, for example, 100 molecules of a particular nucleic acid construct were added and the same amount of IC molecules was added, a 100% isolation efficiency would result in the same signal (after amplification) for both the nucleic acid construct and the IC. If the IC signal obtained would be twice as high as the signal obtained for the nucleic acid construct the efficiency of the nucleic acid isolation procedure was only 50% (meaning that half of the nucleic acid molecules originally present were lost in the isolation procedure). The threshold value can now be adjusted accordingly, thus lowering the risk of obtaining false-negative test results.

More than one nucleic acid construct is added, each nucleic acid construct in a different known quantity. Preferably the nucleic acid constructs are added in a range of amounts, differing from each other by a constant factor (e.g. a factor 10). For example, when three nucleic acid constructs are used, QA, QB, and QC, $10^2$ molecules of QA $10^3$ molecules of QB and $10^4$ molecules of QC, may be added to the sample.

The sample may also be subdivided in more than one reaction aliquots, each of a known volume, to each of which nucleic acid constructs are added in different ranges of amounts. Preferably, in that case, to each reaction volume the same nucleic acid constructs are added. If, for example, two reactions are used, a "low-range" reaction and a "high range" reaction can be carried out. For example, when the ranges of nucleic acid constructs would overlap, to the low-range reaction volume QA, QB, and QC may be added in the quantities as mentioned before, while to the high-range reaction volume $10^4$ $10^5$ and $10^6$ molecules of, QA, QB and QC are added respectively. The ranges of amounts of nucleic acid constructs may overlap but there can also be a gap between the amounts of nucleic acid constructs in the low range and in the high range respectively. Although the use of more than one reaction volume means that more than one amplification reaction has to be carried out, the saving of work and time compared to the prior art methods for the quantification of nucleic acid is still substantial, since with a minimum of reactions a very broad range of analyte concentrations may be covered.

The advantage of using ranges of amounts of nucleic acid constructs that do not overlap is that the number of constructs used may be reduced, while still a broad range of concentrations can be covered. When the analyte is present in an amount that falls in the gap between the ranges of amounts of nucleic acid constructs, no direct comparison to a signal range originating from nucleic acid constructs present in the sample or reaction aliquot, will be possible. However, the amount of analyte nucleic acid can still be determined since the signal of the analyte nucleic acid will be stronger than the low-range signals and weaker than the high range signals, and the concentration can be calculated with these data.

When, with the method according to the invention different ranges of nucleic acid constructs are added to more than one reaction volume, the sample in which the concentration of analyte nucleic acid is to be determined can be split into different volumes, and the nucleic acid constructs can be added to these volumes, before applying each volume to a nucleic acid isolation procedure. Although each volume will have to be treated separately in an isolation procedure, no corrections have to be made for optional losses of analyte nucleic acid during isolation, since variations in performance are corrected for by the addition of the nucleic acid constructs that undergo exactly the same treatment and suffer form the same variations. Of course, one may also subject the total volume to a nucleic acid isolation procedure and split it into different volumes, to which the ranges of constructs will then be added, afterwards.

A problem that may arise when performing amplification reactions is that samples may get contaminated with nucleic acid molecules originating from other samples that, for example, were tested previously in the same laboratory. This may result in false positive test results or, in the case of quantitative measurements, a false outcome in the calculation of the number of nucleic acid molecules present in the sample.

Contaminations, of samples tested with the method according the present invention, in the range of 10–100 molecules will not alter the internal calibration line and will only effect the calculated amount of molecules of analyte nucleic acid if the contamination consists largely of analyte molecules and the amount of analyte nucleic acid in the sample being tested is less than 100 molecules. Contaminations with about 100–1000 molecules will slightly influence the internal calibration line and will only interfere with the calculation of the amount of analyte nucleic acid molecules present in the sample if the amount of analyte molecules in the sample is less than 1000 molecules. Contaminations with more than 1000 molecules will alter the calibration line and the outcome of the calculation.

With a preferred embodiment of the present invention the contamination of samples with nucleic acid molecules originating from previously tested or other samples can be detected.

Contamination can be detected if, when the method according to the invention is used to test more than one sample, the same nucleic acid constructs are used in all samples and the amounts of each particular nucleic acid construct are varied. For example, when three nucleic acid constructs are used (Qa, Qb and Qc), to sample "A" these constructs may be added in the following amounts: $Qa_{high}$ $Qb_{middle}$ and $Qc_{low}$. To sample "B" the same constructs may now be added in the amounts $Qa_{low}$, $Qb_{high}$, $Qc_{middle}$, while to samples "C" the following amounts are added: $Qa_{middle}$, $Qb_{low}$, $Qc_{high}$, etc. Of course the same formulation of nucleic acid constructs may also be used for more than one sample, for example 10 samples in row, before switching to the use of another formulation.

Up to six variations can be made, when three constructs are used, before the same formulation of nucleic acid constructs has to be used again. When four constructs are used up to twenty-four variations can be made etc. The use of different formulations of nucleic acid constructs in different samples will make a contamination, with nucleic acid material originating from a sample for which a different formulation was used detectable. The contamination will alter the internal calibration line in the sample under investigation; the calibration line will have another slope and a low correlation coefficient compared to normal data and will therefore be distinguishable as a contamination.

If, in each sample, a zero level of one of the constructs is used (and the construct for which a zero level is used varies per sample) even very low amounts of contaminating molecules can be detected. It is evident that the presence of a detectable amount of a particular construct of which a zero amount was added, indicates that this particular sample was contaminated with material from a sample for which a different formulation had been chosen.

The detection of the nucleic acid constructs and the analyte nucleic acid after amplification can be performed in different ways. Many detection procedures that are known in the art can be used, as long as a measurable signal is generated that differs according to the amount of amplified nucleic acid (construct or analyte) which the signal represents. Detection methods that can be used with the method according to the invention include methods based on enzymatic and luminescent (fluorescent, electro-chemiluminescent, fosforescent) phenomena as well as detection methods using solid labels like, for example, gold or dye sols and detection methods based on agglutination.

The concentration of analyte nucleic acid present in the sample can be calculated from the relative amounts of analyte nucleic acid and nucleic acid constructs that are represented by the signals generated during the detection procedure.

For example, the logarithm of the ratio between the signals representing the construct (Q) and analyte (A) sequences, log (Q/A), is a linear function of the logarithm of the amount of construct added to the sample, log (Q-input). When the log (Q/A) is plotted as a function of Q(input) a linear graph should be obtained, where the amount of analyte nucleic acid can easily be obtained from the intersection of the straight line with the X-axis. (Provided that the amount of analyte nucleic acid lies near the range of amounts of nucleic acid constructs added.)

Another embodiment of the present invention comprises a method for the quantification of analyte nucleic acid in a panel of test fluids, comprising the dilution of a quantity of said test fluids by a known factor. Samples can now be taken from said diluted test fluids containing an amount of analyte nucleic acid expected to be within a certain range. When the amount of analyte nucleic acid in each one of a panel of test-fluids is to be determined, the complete panel can be pre-diluted to a concentration that is expected to be within this range. The pre-dilution should be carried out in such a way that most of the samples will fall within said range, while the remaining samples will all have a concentration below or will all have a concentration above said range. After the dilution step the complete panel may be subjected to the method according to the invention as described above, wherein the amounts of nucleic acid constructs added to the samples are within said range.

Remaining test-fluids taken from the panel that are below said range (or above) can be tested again with another adjusted dilution or undiluted samples. The advantage of this method is that less amplification reactions are needed than with the previous described high/low range separation.

In another embodiment of the method for the quantification of analyte nucleic acid in a sample according to the invention to a sample a quantity of a nucleic acid construct may be added, said quantity expected to be within the same range as the expected amount of analyte nucleic acid present in said sample, subjecting the sample to a nucleic acid amplification procedure, using amplification reagents capable of reacting with both the analyte nucleic acid and the nucleic acid construct, detecting the relative amount of amplificates derived from analyte nucleic acid and the nucleic acid construct and estimating the amount of analyte nucleic acid present in said sample from said relative amount. After this estimation has been made a second sample from the same test fluid can be subjected to the method according to the invention as described above wherein the amounts of nucleic acid constructs added are within the same range as the estimated amount of analyte nucleic acid present in the first sample.

The advantage of this procedure is that the range of amounts of constructs used can be chosen rather narrow, which will increase the accuracy of the method, and will lower the amount of amplification reactions that has to be carried out even further.

Figure 1A:
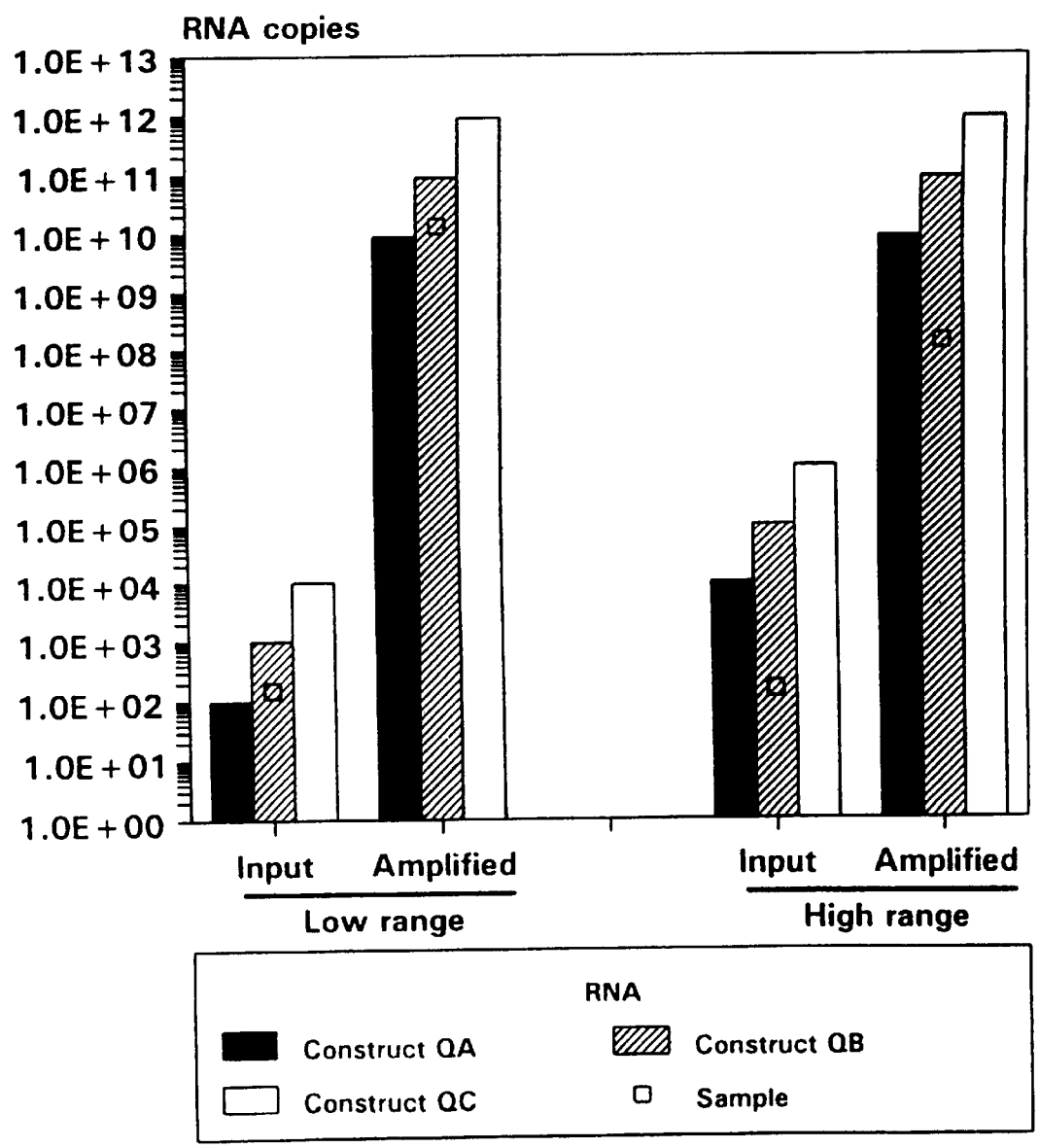
FIG. 1A: Input and amplified amounts of both nucleic acid constructs and sample (analyte) nucleic acid for experiment 1 as decribed in Example 1.
Figure 1B:
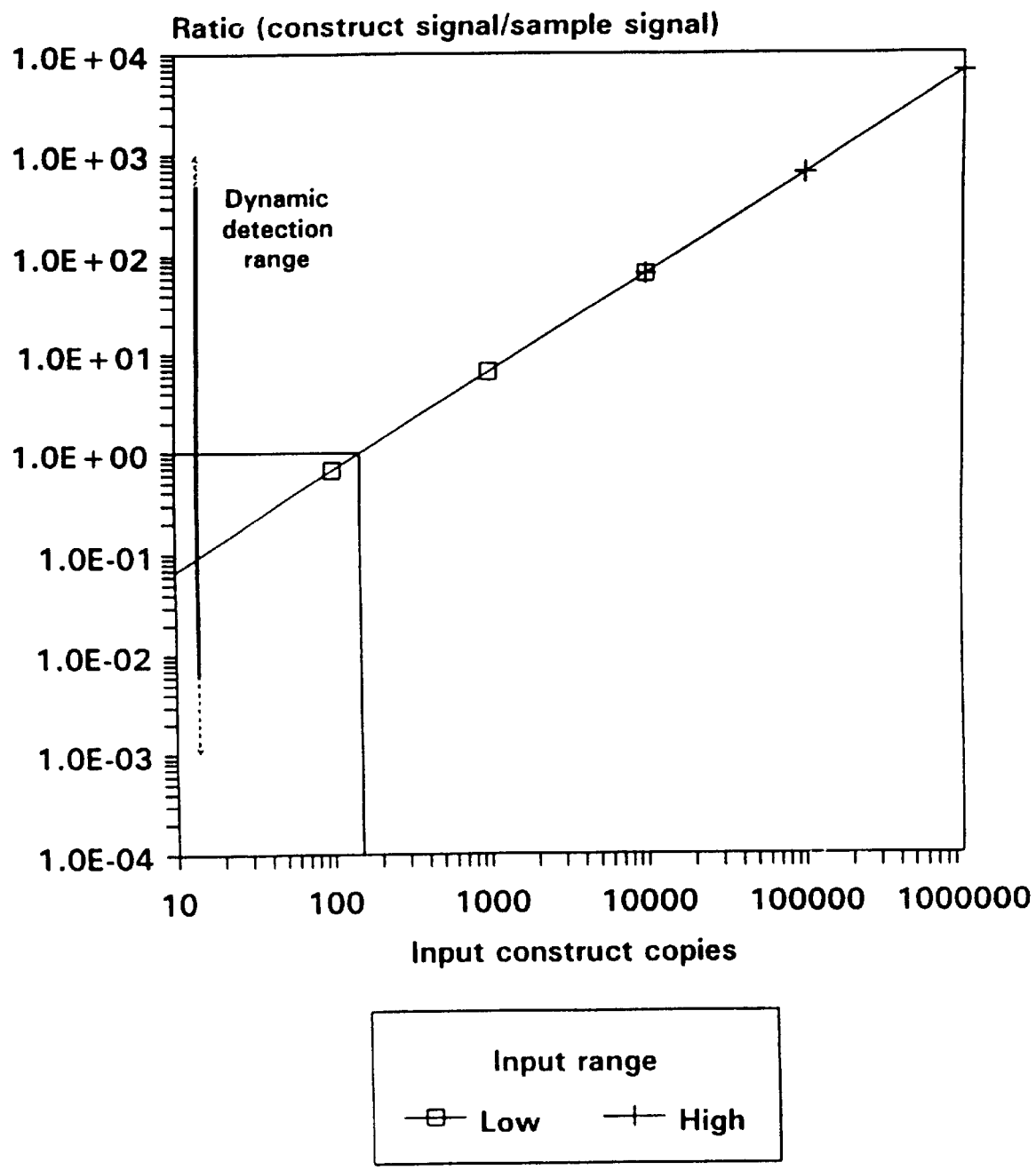
FIG. 1B: Ratio of construct-signal and sample-signal plotted on a logarithmic scale against the amount of input construct copies as used in experiment 1 described in Example 1. The amount of analyte nucleic acid is indicated on the x-axis by the vertical line in the graph.
Figure 2A:
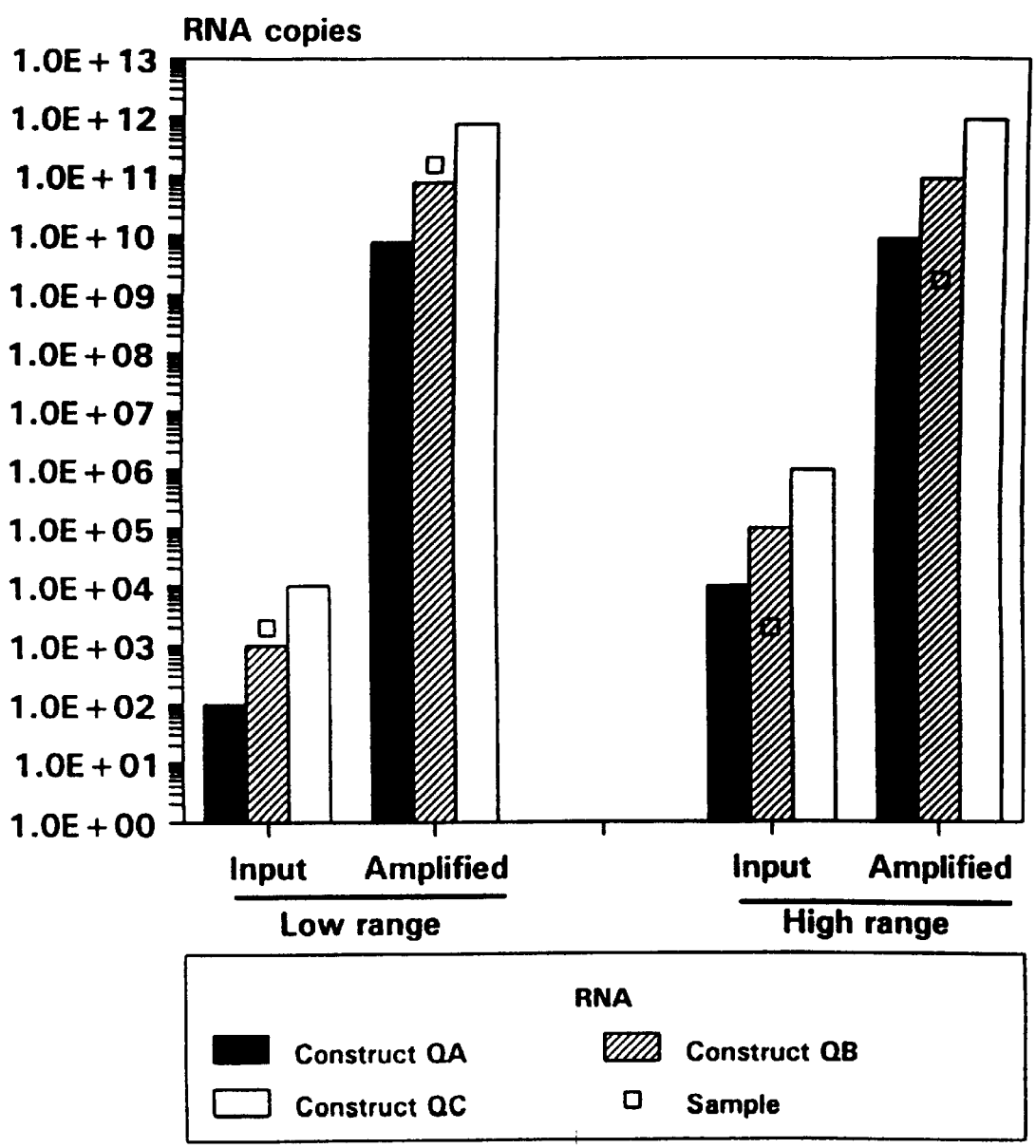
FIG. 2A: Input and amplified amounts of both nucleic acid constructs and sample (analyte) nucleic acid for experiment 2 as decribed in Example 1.
Figure 2B:
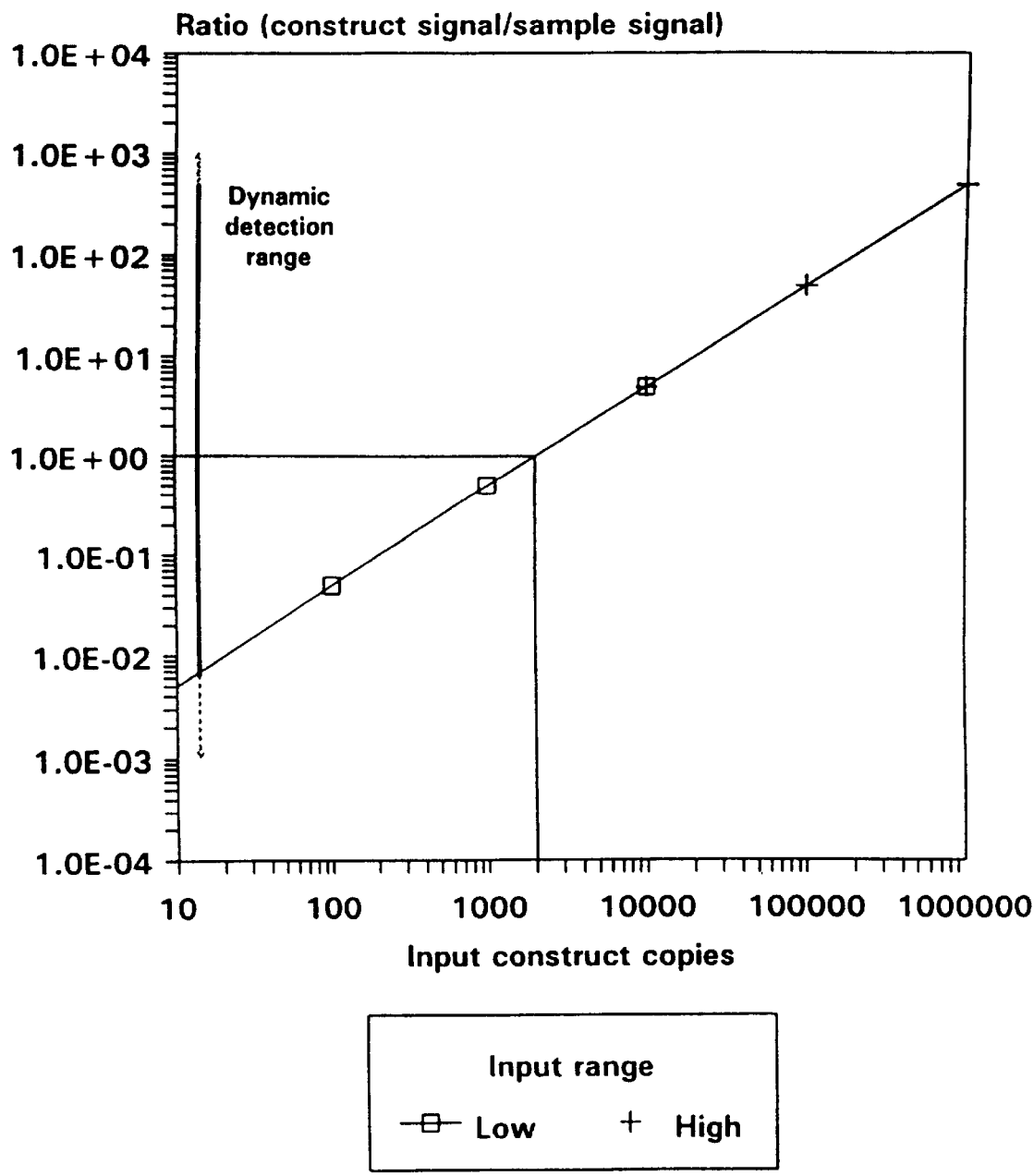
FIG. 2B: Ratio of construct-signal and sample-signal plotted on a logarithmic scale against the amount of input construct copies as used in experiment 2 described in Example 1. The amount of analyte nucleic acid is indicated on the x-axis by the vertical line in the graph.
Figure 3A:
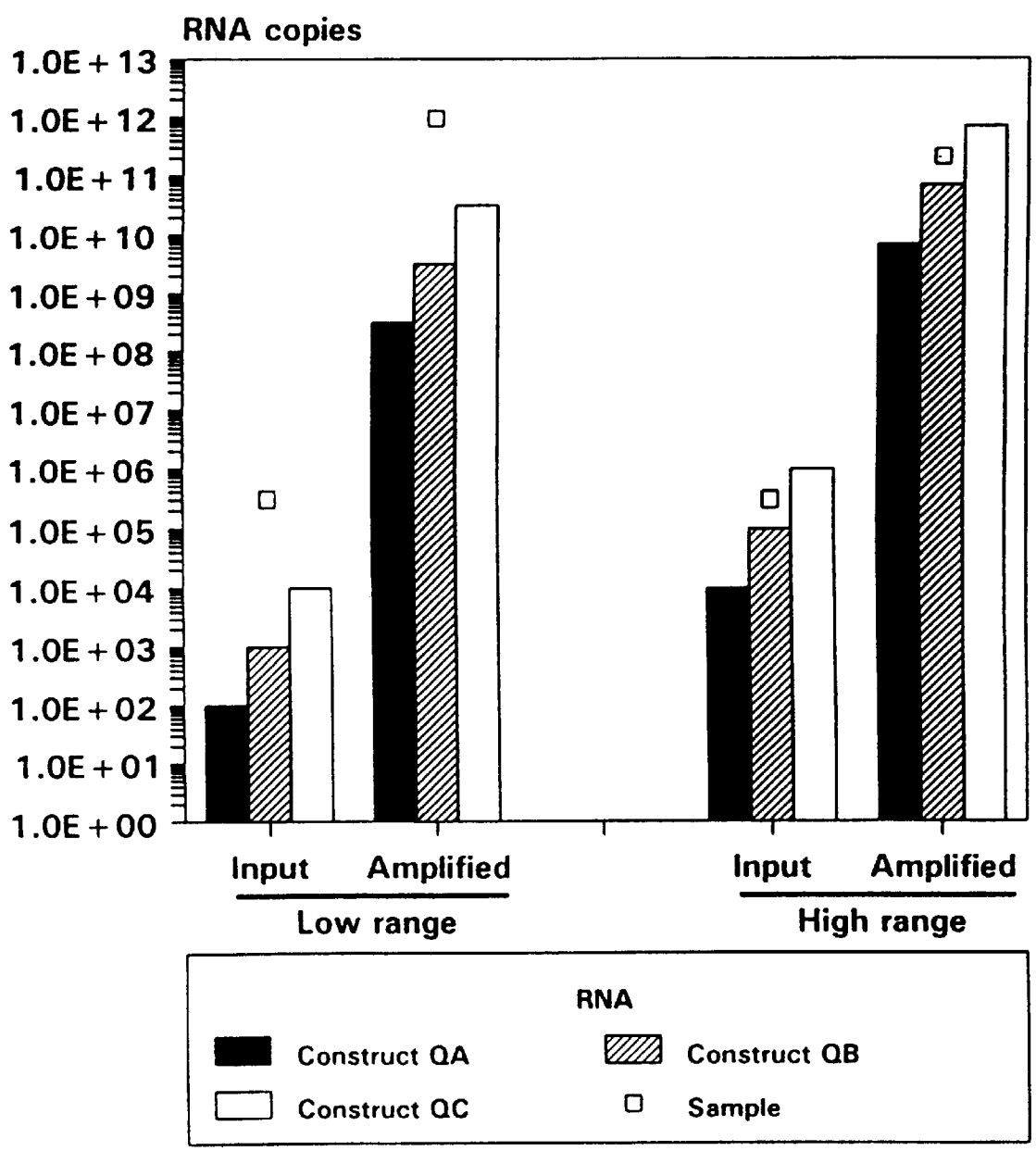
FIG. 3A: Input and amplified amounts of both nucleic acid constructs and sample (analyte) nucleic acid for experiment 3 as decribed in Example 1.
Figure 3B:
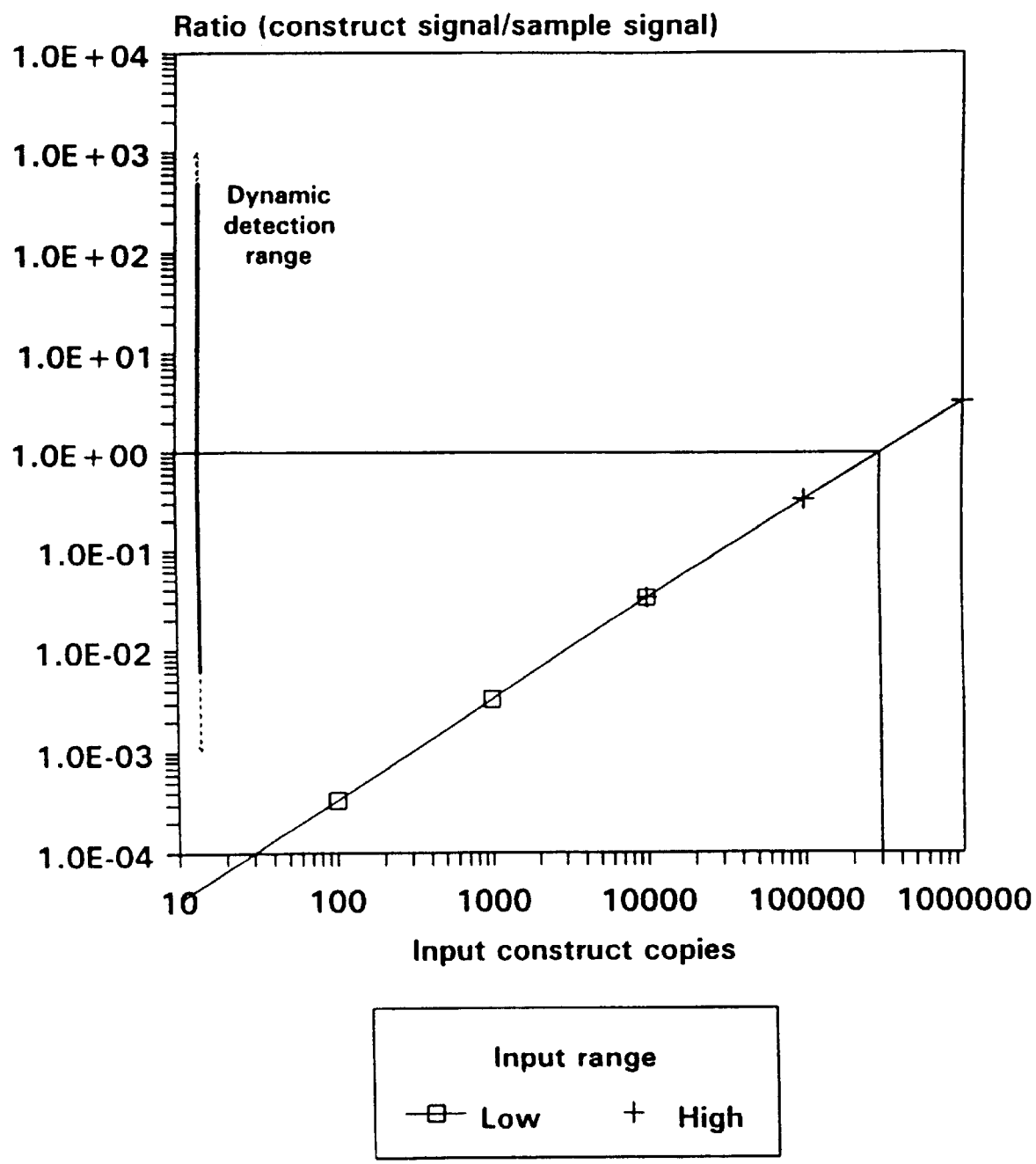
FIG. 3B: Ratio of construct-signal and sample-signal plotted on a logarithmic scale against the amount of input construct copies as used in experiment 3 described in Example 1. The amount of analyte nucleic acid is indicated on the x-axis by the vertical line in the graph.
Figure 4A:
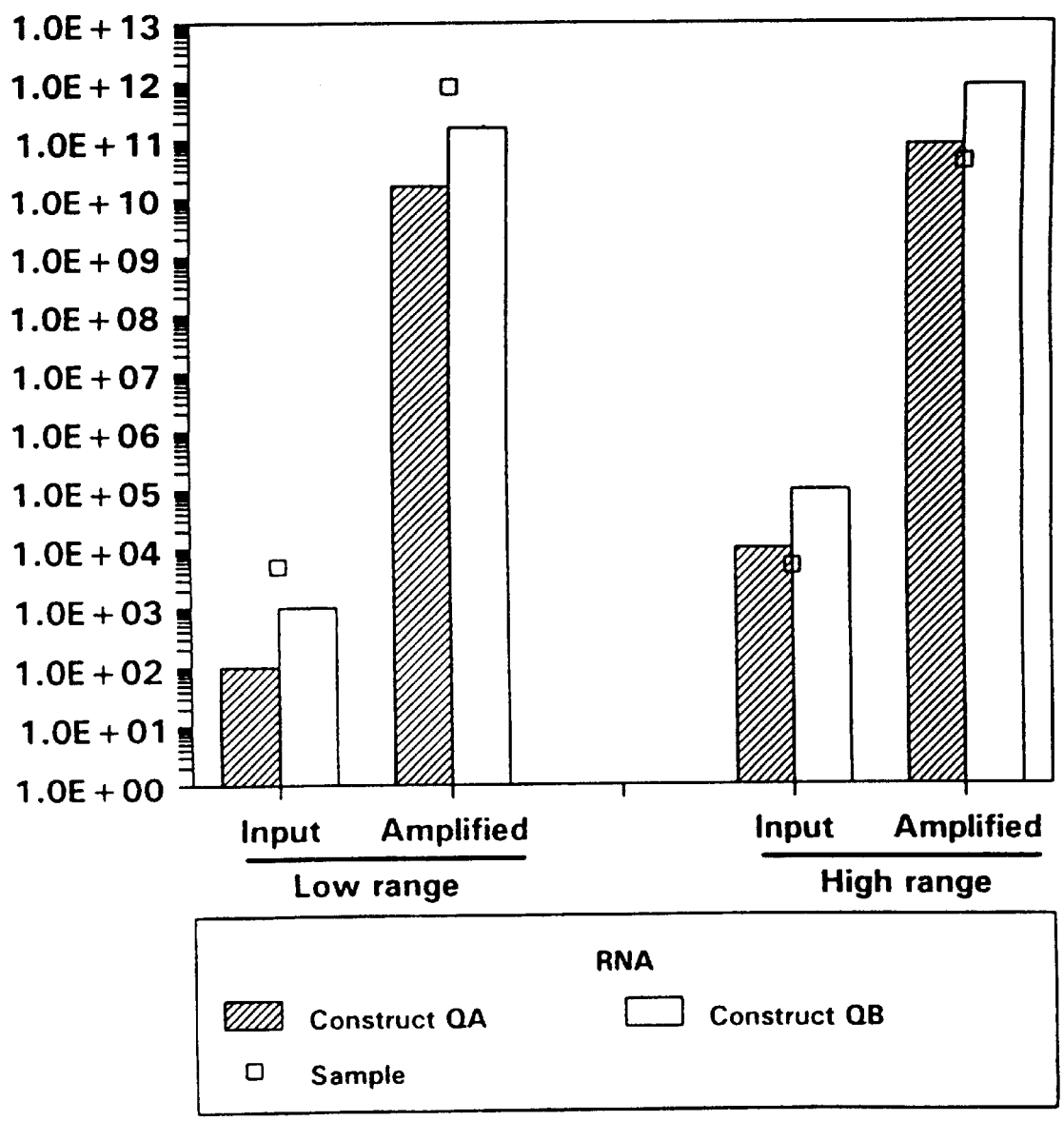
FIG. 4A: Input and amplified amounts of both nucleic acid constructs and sample (analyte) nucleic acid for experiment 4 as decribed in Example 1.
Figure 4B:
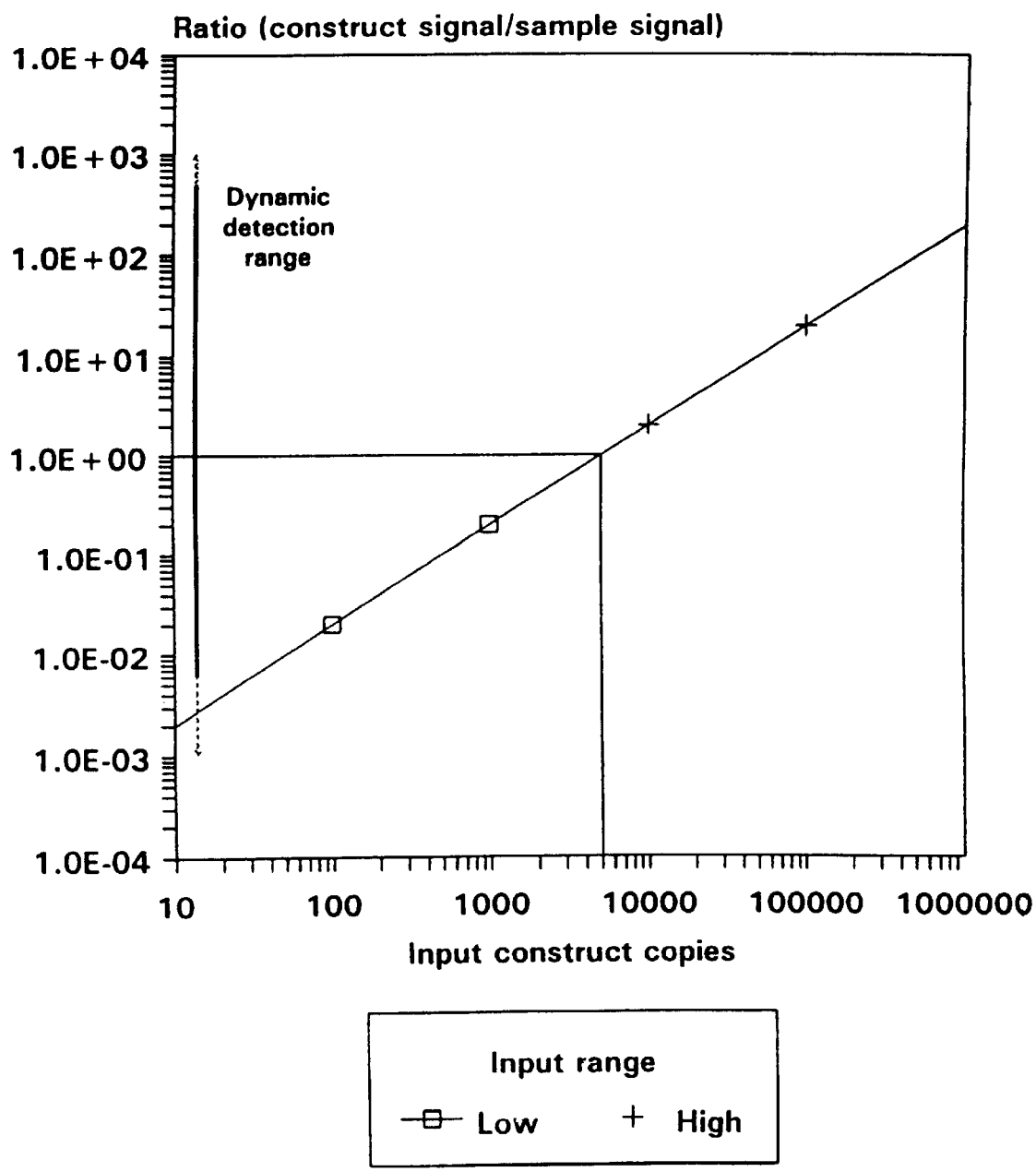
FIG. 4B: Ratio of construct-signal and sample-signal plotted on a logarithmic scale against the amount of input construct copies as used in experiment 4 described in Example 1. The amount of analyte nucleic acid is indicated on the x-axis by the vertical line in the graph.
Figure 5A:
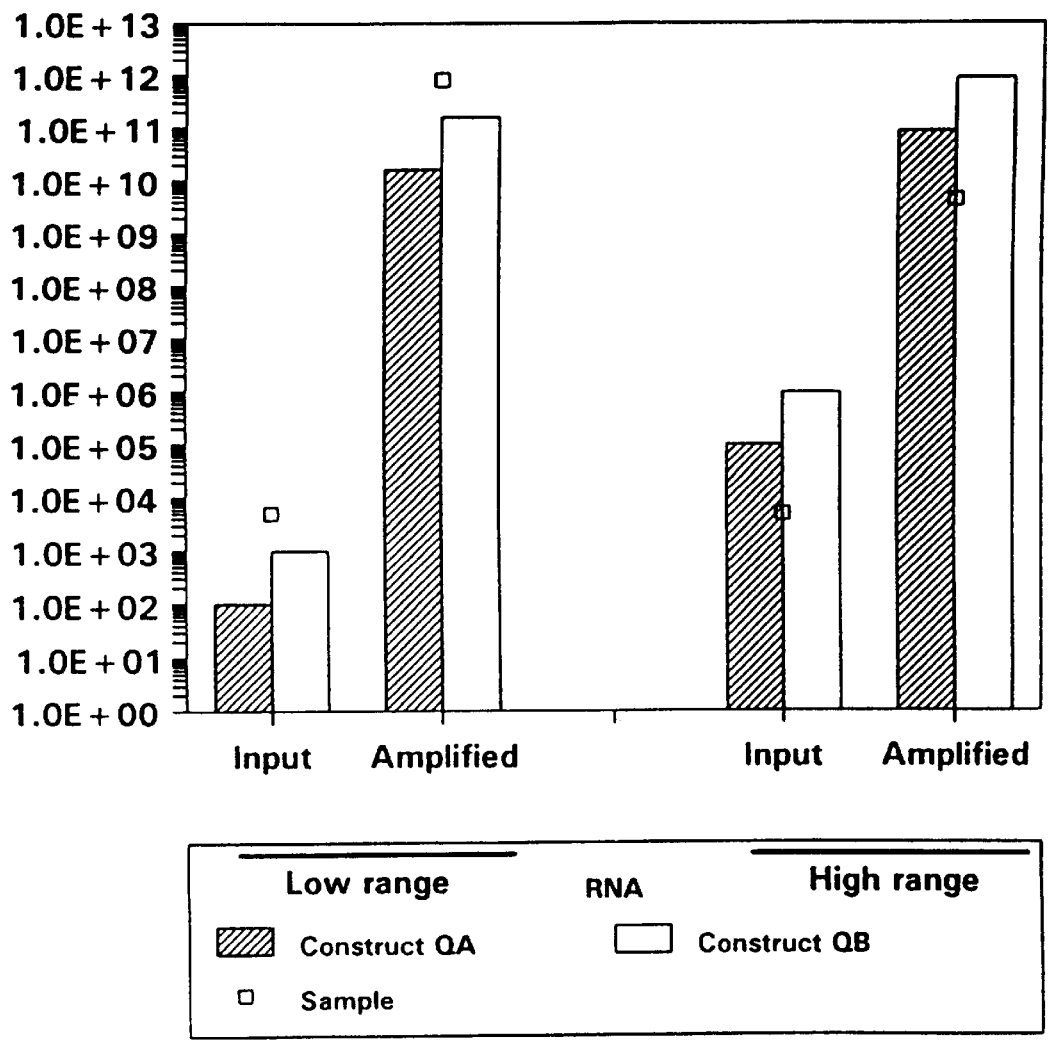
FIG. 5A: Input and amplified amounts of both nucleic acid constructs and sample (analyte) nucleic acid for experiment 5 as decribed in Example 1.
Figure 5B:
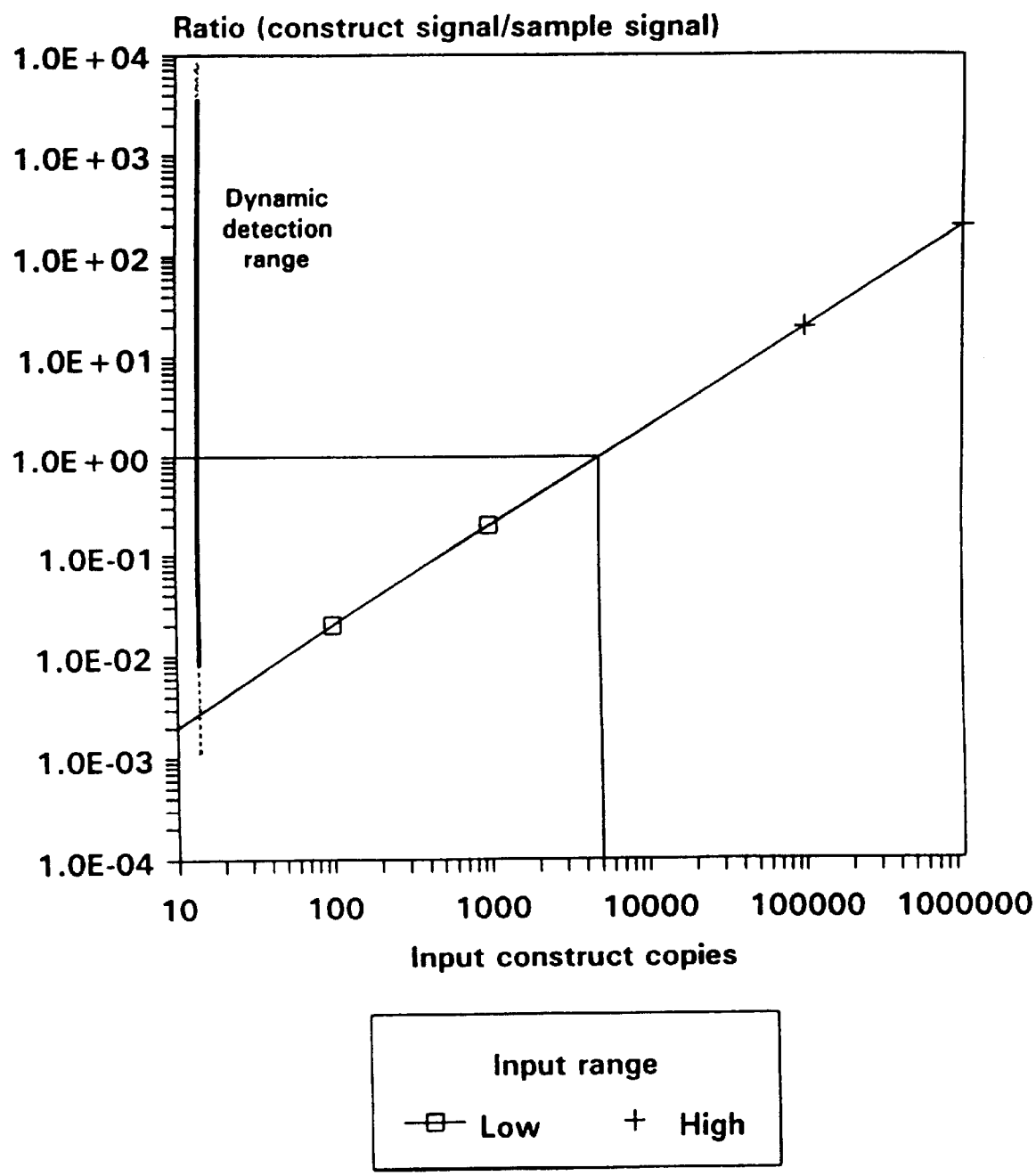
FIG. 5B: Ratio of construct-signal and sample-signal plotted on a logarithmic scale against the amount of input construct copies as used in experiment 5 described in Example 1. The amount of analyte nucleic acid is indicated on the x-axis by the vertical line in the graph.

The present invention is further exemplified by the following examples:

EXAMPLES

Example 1

The following are theoretical examples of a quantitative assay and subsequent detection performed according to the method of the present invention. From these experiments it can be seen how an assay according to the present invention may be performed, as well as the results that would be generated.

Five experiments that may be performed with the method according to the present invention are outlined below. The experiments differ in the amount of input analyte nucleic acid molecules and the ranges of nucleic acid constructs added prior to amplification.

The amounts of input analyte and input constructs are indicated in the table (table 1) given below:

TABLE 1

Amounts of input analyte and construct nucleic acid for experiment 1–5.

| | Analyte Input | Low range Q Input | High range Q Input |
|---|---|---|---|
| Experiment 1: | 150 | QA: 100 | QA: 10000 |
| | | QB: 1000 | QB: 100000 |
| | | QC: 10000 | QC: 1000000 |
| Experiment 2: | 2000 | QA: 100 | QA: 10000 |
| | | QB: 1000 | QB: 100000 |
| | | QC: 10000 | QC: 1000000 |
| Experiment 3: | 300.000 | QA: 100 | QA: 10000 |
| | | QB: 1000 | QB: 100000 |
| | | QC: 10000 | QC: 1000000 |
| Experiment 4: | 5000 | QA: 100 | QA: 10000 |
| | | QB: 1000 | QB: 100000 |
| Experiment 5: | 5000 | QA: 100 | QA: 100000 |
| | | QB: 1000 | QB: 1000000 |

As can be seen from this table, in the first three theoretical experiments three constructs are added (QA, QB and QC, respectively) and two amplification reactions are carried out with a "low range" of construct amounts and a "high range"

of construct amounts. In these experiments the low range and high range do overlap. The overlapping point in these two ranges can be used to compare the amplifications. (If the amplifications are performed in the same way the signals generated should be the same for the overlapping amount of construct in the two ranges). In experiment four and five two ranges of amounts of constructs are used as well, but the low range and the high range do not overlap. Consequently the amount of constructs used per amplification reaction may be reduced, while the same total range of amounts will still be covered.

The amplification rate of the Q-RNAs (constructs) and Wild-type RNA is the same since the RNAs are of the same size, differing only in a sequence of 20 randomized nucleotides, and the same primers and enzymes are used for the amplification. Therefore the initial ratio of the amount of each construct RNA and the amount of Wild-type RNA will not change during amplification. In the detection procedure following the amplification each amplificate mixture is split into four assays for the detection of Wild-type, QA, QB or QC RNA-amplificate. (The amplificate mixtures of experiment four and five only need to be split in three assays.)

If the log ratio of the construct signal and wild type signal is expressed against the logarithm of the input amount of construct RNA, a straight line is expected. The amount of wild type RNA can be calculated from this line. The results that can be obtained with the above described experiments are depicted in FIGS. 1 to 5.

In the first graph of each figure, (a), the amounts of the different constructs, prior and after amplification, are presented, while the amount of analyte nucleic acid is indicated as well.

The second graph of each figure, (b), shows a graph wherein the log ratio of the expected construct signals and the analyte signal (sample signal) is expressed as a function of logarithm of the input amounts of constructs. The amount of analyte input nucleic acid molecules can be derived form these graphs, and follows from the logarithm of the input value (as depicted on the horizontal axis) belonging to the point on the vertical axis where the ratio is equal to 1.

Example 2

A mixture of quantified amounts of construct HIV-1 gag1 RNA transcript was made, comprising respectively 200, 2000 and 20000 copies of three nucleic acid constructs, QA, QB and QC. Quantified amounts of five different wild-type HIV-1 gag1 transcripts, respectively 200000, 20000, 2000, 200, 20 copies and a blank, were mixed with the mixture of Q construct RNAs.

Six amplification reactions, one for each amount of wt-RNA were performed according to a standard protocol. (T. Kievits et al).

From each amplificate 5 μl was diluted to 100 μl with a TBE buffer (90 mM Tris-Borate, 1 mM EDTA pH 8.4). From each dilution 5 μl was added to a tube containing 15 μl of a mixture of 3 pmol biotin-oligo, for capturing of all amplificates, 3 pmol of different tris(2,2'-bipyridine) Ruthenium II chelate labelled oligonucleotides, each comprising a specific sequence for either the wild-type RNA amplificates or one of the construct (QA, QB or QC) amplificates and 20 μg streptavidin coated magnetic dynal beads M280 in a 6.67×SSC buffer (0.75M NaCl, 0.075M Sodiumcitrate pH 7–8).

Four hybridization assays for WT, QA, QB or QC detection were performed on one amplificate. The mixtures were hybridized for 30 minutes at 41° C. and mixed every 10 minutes. 300 μl of assay buffer for electrochemiluminescent ECL detection using the ORIGEN 1.5 detection system of IGEN was added and mixed.

The actual detection in the ORIGEN 1.5 detection system was performed according to manufacturers protocol.

Example 3

In this example a Q-NASBA assay in which 3 Q-RNA internal standards were spiked into the WT-RNA sample at amounts of $10^4$, $10^3$, $10^2$ molecules is described. The 3 internal standard RNA molecules were distinguished using specific ECL labelled probes for a 20 nucleotide randomized sequence (Van Gemen et al. J.Virol.Methods. 43, 177–188, 1993), specific for each internal standard. The ratio's of NASBA amplified internal standards and WT-RNA were measured using an ECL detection instrument.

ECL is based on chemiluminescent labels that emit light on the surface of an electrode (Blackburn et al., Clin.Chem. 37, 1534–1539, 1991). Detection of the signal can be quantified with a dynamic range over 5 orders of magnitude using a specifically developed detection instrument. The ECL technology has been adapted for the detection of amplified nucleic acid using ECL-labelled oligonucleotides in hybridization assays (Kenten, J. H. et al. Clin.Chem. 38, 873–879, 1992). Since the specific activities of the WT, $Q_A$, $Q_B$ and $Q_C$ ECL probes are known, the ratio's of WT, $Q_A$, $Q_B$ and $Q_C$ NASBA amplified RNA could be determined from the signal ratios of the respective probes.

The initial amount of WT input RNA was read from the ratio of the WT signal to $Q_A$, $Q_B$ and $Q_C$ signals in the ECL bead-based assay.

The way in which the Q-constructs were prepared and the assay was performed is described in the "materials and methods" section of this example.

The one-tube Q-NASBA protocol with ECL detection was used for quantifying different amounts of in vitro generated WT-RNA. Three different assays were performed using $10^{1.44}$, $10^{2.83}$, $10^{4.23}$ and $10^{4.83}$ initial WT-RNA molecules as input respectively. The Q-NASBA using the ECl bead-based assay was performed 8–10 times for each WT-RNA amount quantitated by mixing the WT-RNA with $10^4$ $Q_A$ RNA molecules, $10^3$ $Q_B$ RNA molecules and $10^2$ $Q_C$ RNA molecules in a single NASBA amplification. The results (mean±SD) of the quantifications performed were $10^{1.54\pm0.23}$, $10^{2.68\pm0.21}$, $10^{4.16\pm0.20}$ and $10^{4.81\pm0.23}$ using $10^{1.44}$, $10^{2.83}$, $10^{4.23}$ and $10^{4.83}$ initial WT-RNA molecules as input, respectively.

Figure 6:
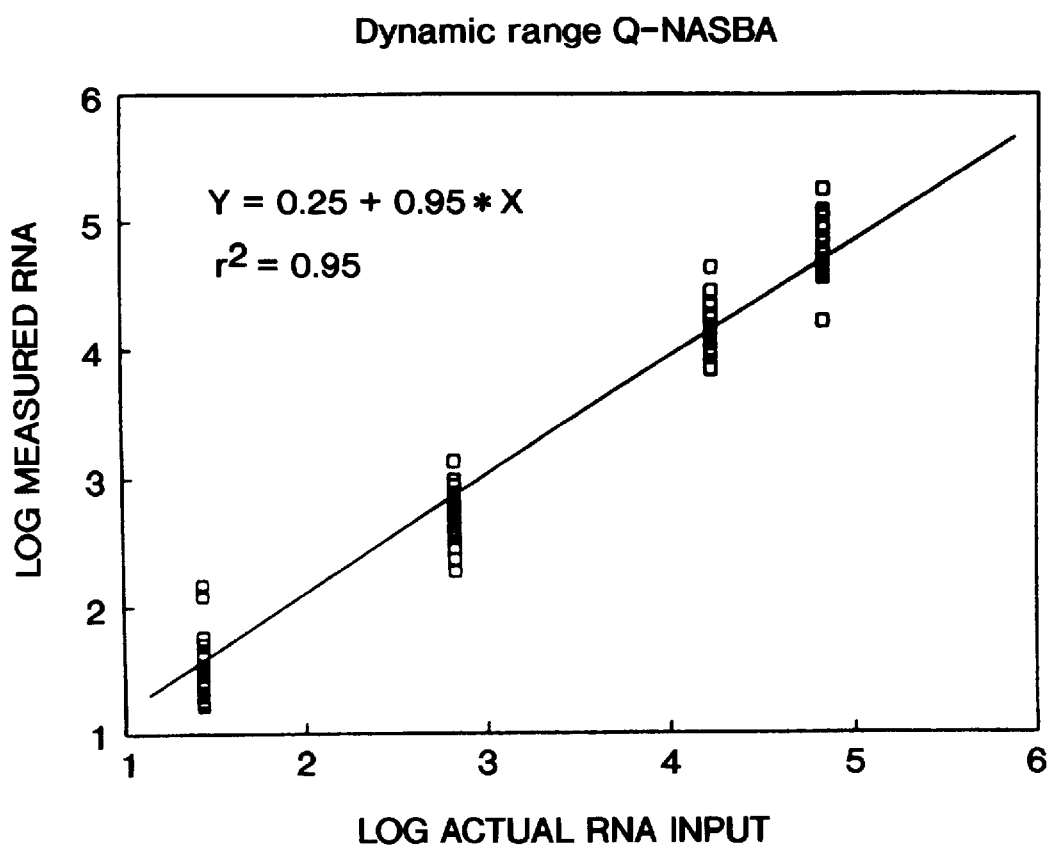
FIG. 6: Dynamic range of the one-tube Q-NASBA. For input of quantification $10^{1.44}$, $10^{2.83}$, $10^{4.23}$ and $10^{4.83}$ in vitro generated WT-RNA molecules were used. The quantification of every WT-RNA amount was performed 8–10 times. $Q_A$, $Q_B$ and $Q_C$ RNA were used at amounts of $10^4$, $10^3$ and $10^2$ RNA molecules, respectively

The results of the assays performed are depicted in FIG. 6. As can be seen from this figure the WT-RNA amount can be quantitated reliably to 1/10 of the lowest Q-RNA amount used in the one tube quantification protocol.

MATERIALS AND METHODS

Plasmids and RNA synthesis

Genetic and recombinant DNA techniques followed standard procedures (Sambrook, J. et al., Molecular cloning. A laboratory manual, Cold Spring Harbor, N.Y.:Cold Spring Harbor Lab., 1989. Ed. 2nd. The plasmid pGEM3RAN (Van Gemen et al.1993) with a 22 nucleotide randomized sequence (pos. 1429–1451 HIV-1 pv22 sequence, (Muesing, M. A. et al., Nature 313, 450–458, 1985) was used to delete the Acc I sit in multiple cloning site and part of the HIV-1 cloned sequence (pos 1691 to 2105 HIV-1 pv22) for reasons not related to the quantitative NASBA amplification. In this plasmid the randomized sequence was replaced by 5'ATG-.CAA.GGT.CGC.ATA.TGA.GTA.A3' or 5'ATA.AG-C.ACG.TGA.CTG.AGT.ATG.A3' to create pGEM3Q$_B$δgag3 and pGEMQ$_C$δgag3 respectively. Plasmid pGEM3RAN was renamed pGEM3Q$_A$. In vitro RNA was generated from pGEM3p24 (WT-RNA), pGEM3Q$_A$ ($Q_A$-RNA), pGEM3Q$_B$δgag3 ($Q_B$-RNA) and pGEM3Q$_C$δgag3 ($Q_C$-RNA) using SP6 RNA polymerase (Sambrook, 1989).

The cloned inserts of pGEM3p24 and pGEM3$Q_A$ were recloned into vector pGEM4 creating pGEM4p24 and pGEM4$Q_A$. Using these plasmids in vitro RNA was made using T7 RNA polymerase (Sambrook, 1989). The length of the in vitro RNA is 1514 nucleotides for plasmids pGEM3p24 (WT-RNA) and pGEM3$Q_A$ ($Q_A$-RNA) and 1090 nucleotides for plasmids pGEM3$Q_B$δgag3 ($Q_B$-RNA) and pGEMQ$_C$δgag3 ($Q_C$-RNA). The RNA was treated with DNase to remove plasmid DNA and purified on an anionic exchange column (Qiagen). The in vitro RNA was quantitated spectrophotometrically and diluted to desired concentrations with water. All RNA solutions were stored at −20° C.

Nucleic acid isolation

Nucleic acids were isolated from plasma according to the method of Boom et al. (Boom, R., et al., J.Clin.Microbiol. 28, 495–503, 1990; Van Gemen et al.1993). Nucleic acid of 100 μl plasma was finally resuspended in 100 μl water and stored at −70° C.

NASBA

All enzymes were purchased from Pharmacia, except AMV-reverse transcriptase which purchased from Seikagaku. BSA was purchased from Boehringer Mannheim. Twenty-three μl NASBA reaction mixtures (final concentration in 25 μl reaction mixture: 40 mM tris, pH 8.5, 12 mM MgCl$_2$, 42 mM KCl, 15% $^{v/v}$ DMSO, 1 mM each dNTP, 2 mM each NTP, 0.2 μm Primer 1: 5' AAT.TCT.AAT.AC-G.ACT.CAC.TAT.AGG.GTG.CTA.TGT.CAC.TTC.CCC.TTG.GTT.CTC.TCA, 0.2 μm primer 2: 5' AGT.GGG.GGG.ACA.TCA.AGC.AGC.CAT.GCA.AA, 0.2–2 μl wild-type RNA and 2 μl in vitro Q-RNA; (Kievits, T. et al. J.Virol.Methods. 35, 273–286, 1991; Van Gemen et al.1993) were incubated at 65° C. for 5 minutes to allow destabilization of secondary structures in the RNA and subsequently cooled down to 41° C. to allow primer annealing. The amplification was started by adding 2 μl enzyme mixture (0.1 μg/μl BSA, 0.1 Units RNase H, 40 Units T7 RNA polymerase and 8 Units AMV-reverse transcriptase). Reactions were incubated at 41° C. for 90 minutes. For every quantitation 2 negative controls were added.

Enzymatic bead-based detection

To detect and determine the ratio of NASBA amplified WT and $Q_A$ RNA in the earlier described quantification protocol (Van Gemen et al.1993) a bead-based enzymatic assay was developed. One hundred μl of 2.8 μm polystyrene paramagnetic beads (Dynal Inc., Great Neck, N.Y., USA) coated with streptavadin were washed twice with 200 μl 1×PBS, 0.1% BSA and resuspended in 100 μl 1×PBS, 0.1% BSA. The washed beads were incubated 1 hr at room temperature with 300 pmol of a HIV-1 specific, biotinylated capture probe (5' TGT.TAA.AAG.AGA.CCA.TCA.ATG.AGG.A) and subsequently washed once with 200 μl 5×SSPE, 0.1% SDS and once with 200 μl 1×PBS, 0.1% BSA. The beads were resuspended in 100 μl, 1×PBS, 0.1% BSA.

Five μl beads, 5 μl NASBA reaction mixture and 50 μl hybridization buffer (5×SSPE, 0.1% SDS, 0.1% blocking reagent, 10 μg/ml Salmon sperm DNA) were incubated for 30 minutes at 45° C. The beads were washed twice with 100 μl 2×SSC, 0.1% BSA followed by an incubation with 5×10$^{-7}$ μmol WT or Q detection oligonucleotide probe, of which 10% was HRP labelled, in 50 μl hybridization buffer for 30 minutes at 45° C.

The bead-capture oligonucleotide-NASBA amplified WT or $Q_A$ RNA-detection probe complex was washed once with 100 μl 2×SSC, 0.1% BSA, once with 100 μl TBST and twice with 100 μl TBS. Subsequently, 100 μl colour substrate (TMB/peroxide solution) was added to the beads and incubated for 3 minutes at room temperature.

The colour reaction was stopped by addition of 50 μl 250 mM oxalate. The absorbance of the 150 μl colour reaction was read at 450 nM in a micro-plate reader (Micro SLT 510, Organon Teknika, Boxtel, The Netherlands).

The absorbance values were corrected for background signal (i.e. negative controls) and the signal calculated as the percentage of the signal obtained by independently amplified WT or $Q_A$ RNA.

ECL Bead-based Detection

Five μl of NASBA amplified RNA (WT, $Q_A$, $Q_B$ and $Q_C$) diluted 20 times in water was incubated with 20 μl (3.3 pmol) of the HIV-1 specific, biotinylated capture probe (see enzymatic bead based detection), 3.3 pmol of an ECL (tris [2,2-bipyridine] ruthenium [II] complex) labelled oligonucleotide probe, specific for either WT, $Q_A$, $Q_B$ or $Q_C$ NASBA amplified RNA and 20 μg (2 μl) of streptavidin coated magnetic beads in 5×SSC for 30 minutes at 41° C. During the incubation the tubes were mixed every 10 minutes by vortexing. Subsequently, 300 μl of TPA solution (100 mM tripropylamine, pH=7.5) was added and the hybridization mixture was placed in an Origen 1.5 ECL detection instrument (Organon Teknika, Boxtel, The Netherlands).

Example 4

Figure 7:
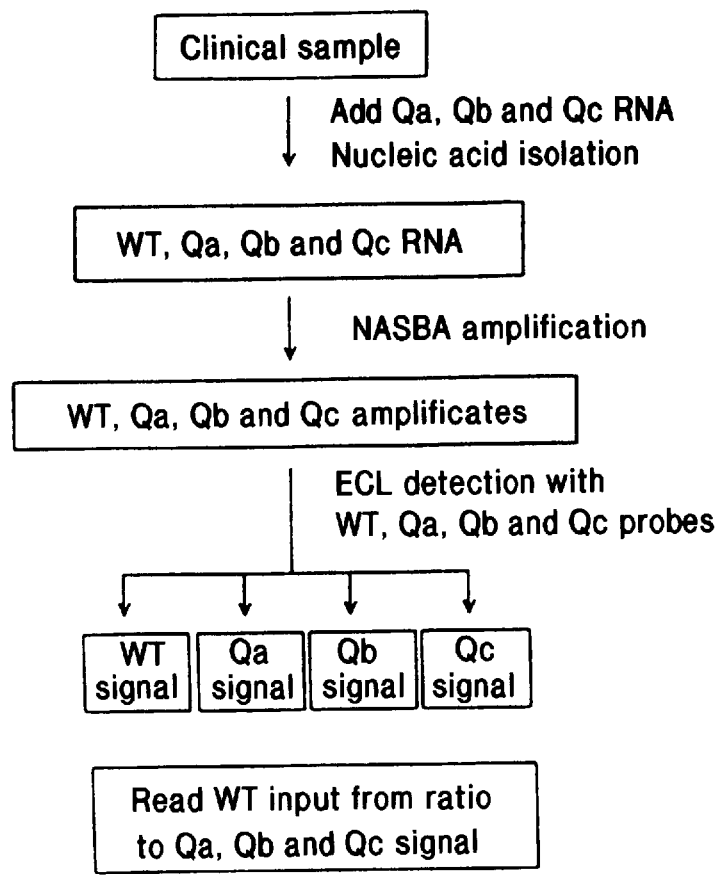
FIG. 7: Schematical flow-chart of the one-tube Q-NASBA with addition of $Q_A$, $Q_B$ and $Q_C$ internal standard RNAs before nucleic acid isolation in the lysis buffer.

The efficiency of the nucleic acid isolation can influence the outcome of the WT-RNA quantification. To circumvent the influence of loss of nucleic acid during the isolation, the $Q_A$, $Q_B$ and $Q_C$ RNA's can be added before or during the first step of the nucleic acid isolation (FIG. 7). This principle was tested using 10$^4$ molecules in vitro generated WT-RNA and HIV-1 RNA isolated from an in vitro cultured viral stock solution. In vitro generated WT-RNA and the HIV-1 viral stock RNA were re-isolated with and without the addition of $Q_A$, $Q_B$ and $Q_C$ RNA during the first step of the nucleic acid isolation (i.e. in the lysis buffer).

The methods used are described in the "materials and methods" section of example 3.

When originally isolated WT-RNA and HIV-1 viral stock RNA were quantified by the addition of $Q_A$, $Q_B$ and $Q_C$ during the amplification (i.e. control quantifications) the outcome was 3.3×10$^4$ and 2.1×10$^4$ for in vitro generated WT-RNA and HIV-1 viral stock RNA respectively. Quantification of the re-isolated RNA with addition of $Q_A$, $Q_B$ and $Q_C$ RNA before the re-isolation procedure revealed 2.5×10$^4$ and 1.5×10$^4$ for in vitro generated WT-RNA and HIV-1 viral stock RNA respectively. However, when the re-isolated RNA was quantified with addition of $Q_A$, $Q_B$ and $Q_C$ RNA after the re-isolation procedure the outcome was 4.7×10$^3$ and 2.0×10$^3$ for in vitro generated WT-RNA and HIV-1 viral stock RNA respectively. This indicates that the efficiency of re-isolation of RNA was approximately 10%. However, addition of $Q_A$, $Q_B$ and $Q_C$ before the re-isolation resulted in RNA quantifications that were equal to the control quantifications due to a constant ratio of WT:$Q_A$:$Q_B$:$Q_C$ RNA, independent of the absolute amount of nculeic acid isolated.

Results are depicted in Table 2.

Table 2: Comparison of re-isolation of 10$^4$ in vitro generated WT-RNA molecules and an HIV-1 viral stock RNA solution with addition of $Q_A$, $Q_B$, $Q_C$ RNA during the first step of nucleic acid isolation and after the nucleic acid isolation.

| Additions during NA isolation | Additions [a] after NA isolation | WT-RNA quantitated |
|---|---|---|
| | $10^4$ WT-RNA + $Q_A,Q_B,Q_C$ [b] | $3.3 \times 10^4$ |
| $10^4$ WT-RNA | $Q_A,Q_B,Q_C$ | $4.7 \times 10^3$ |
| $10^4$ WT-RNA + $Q_A,Q_B,Q_C$ | | $2.5 \times 10^4$ |
| | Viral stock RNA + $Q_A,Q_B,Q_C$ [b] | $2.1 \times 10^4$ |
| Viral stock RNA | $Q_A,Q_B,Q_C$ | $2.0 \times 10^3$ |
| Viral stock RNA + $Q_A,Q_B,Q_C$ | | $1.5 \times 10^4$ |

[a] $Q_A$, $Q_B$ and $Q_C$ were added at $10^2$, $10^3$ and $10^4$ RNA molecules, respectively.
[b] Control quantifications with no nucleic acid re-isolation involved.

Example 5

The method according to the invention was compared to earlier described Q-NASBA protocols (Van Gemen et al.1993; Jurriaans et al., submitted, 1993) where only one Q-RNA is used, and, if a dynamic range of 5 logs is to be achieved, at least 6 amplification reactions per clinical (wild-type) sample are necessary, i.e. one positive WT control without addition of internal standard and 5 reactions with an increasing amount ($10^2$–$10^6$) of internal standard RNA molecules.

The number of amplification reactions can be decreased with the method according to the invention where several distinguishable internal standards are spiked into one amplification.

In contrast, when only one Q-RNA is used ($Q_A$) in combination with enzyme labelled probes the initial WT-RNA concentration must be deduced from the ratio of the WT-signal to Q-signal using different concentrations Q-RNA in separate amplifications.

The two methods were compared using model systems and plasma samples of HIV-1 infected individuals.

The one-tube Q-NASBA using $Q_A$, $Q_B$ and $Q_C$ RNA was compared to the earlier described Q-NASBA protocol (Van Gemen et al., 1993) that uses 6 amplifications per quantification by analysing 0.1 ml plasma samples of 3 asymptomatic HIV-1 infected individuals. In the same experiment the difference between addition of $Q_A$, $Q_B$ and $Q_C$ before and after nucleic acid isolation was investigated again (table 3). In cases where the WT-RNA is quantitated by the one-tube Q-NASBA protocol the WT-RNA amount can be quantitated reliably to 1/10 of the lowest Q-RNA amount used in the one tube quantification protocol.

Since the addition of $Q_A$, $Q_B$ and $Q_C$ (at $6 \times 10^5$, $6 \times 10^4$ and $6 \times 10^3$, respectively) is to 0.1 ml plasma when they are added to the lysis buffer, the lower reliable quantification limit is $6 \times 10^2$ RNA copies per 0.1 ml plasma. Addition of $Q_A$, $Q_B$ and $Q_C$ (at $10^4$, $10^3$ and $10^2$, respectively) to the isolated nucleic acid gives a reliable lower quantification limit of $10^3$ RNA copies per 0.1 ml plasma when 1 μl plasma equivalents of nucleic acid are used for amplification. In both cases the WT-RNA amount can be quantitated reliably to 1/10 of the lowest Q-RNA amount used in the one-tube quantification protocol. The protocol using 6 amplifications per quantification with $10^2$ as lowest internal standard Q-RNA amount has a lower reliable quantification limit of $10^4$ RNA copies per 0.1 ml plasma when 1 μl plasma equivalents of nucleic acid are used for amplification. The results indicate that in this particular experiment the efficiency of nucleic acid isolation varied between 100% (patient 1) and 50% (patient 2). Patient 3 was always below the reliable quantification limit, although this limit was most accurate (i.e. the lowest) for the one-tube Q-NASBA assay with addition of $Q_A$, $Q_B$ and $Q_C$ to the lysis buffer before nucleic acid isolation (table 3).

Table 3: Comparison of the one tube Q-NASBA with the quantification protocol using 6 amplifications per quantification on 1 ml plasma samples of 3 HIV-1 infected patients.

| Patient | A | B | C |
|---|---|---|---|
| 1 | $<1.0 \times 10^4$ | $1.5 \times 10^3$ | $1.1 \times 10^3$ |
| 2 | $1.0 \times 10^4$ | $5.6 \times 10^3$ | $1.3 \times 10^4$ |
| 3 | $<1.0 \times 10^4$ | $<1.0 \times 10^3$ | $<6.0 \times 10^2$ |

A: Q-NASBA with 6 amplifications per quantification
B: One-tube Q-NASBA; $Q_{A,B,C}$ added after nucleic acid isolation.
C: One-tube Q-NASBA; $Q_{A,B,C}$ added before nucleic acid isolation.

Example 6

Finally we tested the reproducibility of the one-tube Q-NASBA with addition of $Q_A$, $Q_B$ and $Q_C$ to the lysis buffer before nucleic acid isolation using an in vitro cultured HIV-1 viral stock solution in which the amount of viral particles was quantitated by electronmicroscopy (Layne, S. P. et al., Virology. 189, 695–714, 1992). The HIV-1 viral stock containing $2.9 \times 10^{10}$ viral particles per ml was diluted 10.000 times in water and $Q_A$, $Q_B$ and $Q_C$ (at $6 \times 10^5$, $6 \times 10^4$ and $6 \times 10^3$, respectively) were added to 100 μl diluted viral stock solution, resulting in the measurement of $4.35 \times 10^{10}$ RNA molecules per ml. Results are depicted in Table 4. The mean±SD of the RNA quantification was $10^{10.64 \pm 0.05}$, showing that the accuracy of the one-tube Q-NASBA is within 0.1 log when quantitating this in vitro cultured viral stock solution.

(The procedures followed are described in the Materials and Methods section of example 3).

From table 4 it can be seen that an accuracy of the assay within 0.1 log when quantitating HIV-1 RNA in an in vitro cultured viral stock solution can be achieved with the method according to the invention. This result enables reliable measurements of differences in HIV-1 RNA load of 0.4 logs and greater.

TABLE 4

Reproducibility of the one-tube Q-NASBA. The in vitro cultured HIV-1 viral stock contains 2.9 (±1.6) $\times 10^{10}$ virai particles per ml.

| Nucleic acid isolation | RNA molecules per ml (mean ± std) |
|---|---|
| 1 | $10^{10.69 \pm 0.16}$ a |
| 1 | $10^{10.53 \pm 0.03}$ a |
| 1 | $10^{10.61 \pm 0.03}$ a |
| 2 | $10^{10.64 \pm 0.05}$ a |
| 2 | $10^{10.65 \pm 0.01}$ a |
| 2 | $10^{10.68 \pm 0.02}$ a |
| 3 | $10^{10.64 \pm 0.05}$ b |
| 4 | $10^{10.67 \pm 0.06}$ b |
| 5 | $10^{10.65 \pm 0.07}$ b |

$Q_A$, $Q_B$ and $Q_C$ ($6 \times 10^5$, $6 \times 10^4$ and $6 \times 10^3$, respectively) were added to 100 μl of a 10.000 dilution of the viral stock in water.
[a] duplicate amplifications
[b] triplicate amplifications
The mean ± SD of all quantifications is $10^{10.64 \pm 0.05}$ ($4.35 \times 10^{10}$) RNA molecules per ml.

We claim:

1. A method for the quantification of an unknown amount of an analyte nucleic acid in a sample comprising:
   (a) adding to a predetermined volume of said sample different and known amounts of more than one nucleic acid construct, wherein each construct is separately measurable from the analyte nucleic acid and from one another, each construct is capable of being co-amplified with the analyte nucleic acid, and wherein the constructs and the analyte are amplified with comparable efficiency;
   (b) subjecting the sample from step (a) to a nucleic acid amplification procedure using amplification reagents that react with both the analyte nucleic acid and the nucleic acid constructs;
   (c) detecting the amplification products from step (b) of the analyte nucleic acid and each nucleic acid construct using a detection method that generates a measurable signal; and
   (d) determining the amount of analyte nucleic acid in the sample by comparing the signal of the analyte to the signals of each of the constructs.

2. The method according to claim 1, wherein each nucleic acid construct has the same sequence as the analyte nucleic acid except for a sequence in each nucleic acid construct that is different from the analyte nucleic acid sequence and from each other's sequence, such that the analyte and each construct can be separately measured using different nucleic acid detection probes.

3. The method according to claim 2, wherein the sequence that is different is a randomized sequence comprising about 20 nucleotides.

4. The method according to claim 1, wherein the nucleic acid constructs are added in amounts differing from each other by a constant factor.

5. The method according to claim 4, wherein the amounts of the nucleic acid constructs differ from each other by a factor of 10.

6. The method according to claim 1, wherein prior to step (b) the sample is subjected to a nucleic acid isolation procedure.

7. The method according to claim 6, wherein a known quantity of an isolation control sequence is added to the sample after the sample has been subjected to a nucleic acid isolation procedure.

8. The method according to claim 1, wherein the sample is split into more than one reaction aliquot of known volume, to each of which the same nucleic acid constructs are added to each reaction volume in amounts differing from each other by a constant factor, wherein each reaction aliquot has a different range of amounts of nucleic acid constructs.

9. The method of claim 1, wherein prior to step (a) the amount of analyte is estimated by subjecting a portion of the sample, to which a known quantity of a nucleic acid construct is added, to an amplification reaction, whereby both the analyte and the construct are amplified with the same amplification reagents, detecting each the analyte and the construct using a measurable signal, and comparing the signal of the analyte to the signal of the known amount of construct to thereby obtain an estimate of the amount of analyte nucleic acid in the sample.

10. The method according to claim 8, wherein the different ranges of amounts of constructs between the reaction aliquots do not overlap.

11. The method of claim 1, wherein if more than one sample is tested at the same time, contamination can be detected by using the same nucleic acid constructs in all samples, and varying the amounts of each of the particular nucleic acid constructs, whereby a change in the internal calibration data of the nucleic acid constructs of one or more of the samples as compared to normal data indicates contamination.

12. The method according claim 11, wherein in each sample more than two nucleic acid constructs are used and a zero amount of one of the nucleic acid constructs is used, wherein the construct for which a zero amount is used is different in each sample.

13. A method for the quantification of analyte nucleic acid in a panel of test fluids comprising the steps of:
   diluting a quantity of each fluid in a panel of test fluids by a known factor and taking a sample from each diluted test fluid believed to contain an amount of analyte nucleic acid expected to be within a certain range of amounts, and
   subjecting each sample to the method of claim 1, wherein the amounts of nucleic acid constructs added to each sample are within the same range of amounts as the expected amount of analyte nucleic acid.

14. The method according to claim 13, comprising the additional steps of:

identifying samples containing an amount of analyte nucleic acid lower than the expected range of amounts, subjecting said samples to dilution by a lower factor.

15. The method according to claim 13, comprising the additional steps of:

identifying samples containing an amount of analyte nucleic acid higher than the expected range of amounts, subjecting said samples to dilution by a higher factor.

16. The method of claim 1, wherein in step (a) three nucleic acid constructs are added to the sample.

17. The method of claim 1, wherein the amount of analyte nucleic acid present in the sample is determined by generating a straight line by plotting the logarithms of the ratios of each construct to the analyte versus the logarithms of the known amounts added to the sample of each construct, whereby the point at which the line intersects the X-axis is the amount of analyte present in the sample before amplification.

* * * * *